US012295691B2

(12) United States Patent
Burbank et al.

(10) Patent No.: US 12,295,691 B2
(45) Date of Patent: May 13, 2025

(54) TENSION REGULATOR FOR ACTUATION ELEMENTS, AND RELATED REMOTELY ACTUATED INSTRUMENTS, SYSTEMS, AND METHODS

(71) Applicant: INTUITIVE SURGICAL OPERATIONS, INC., Sunnyvale, CA (US)

(72) Inventors: William A. Burbank, Sandy Hook, CT (US); Gregory W. Dachs, II, San Mateo, CA (US); Bruce M. Schena, Menlo Park, CA (US)

(73) Assignee: INTUITUVE SURGICAL OPERATIONS, INC., Sunnyvale, CA (US)

( * ) Notice: Subject to any disclaimer, the term of this patent is extended or adjusted under 35 U.S.C. 154(b) by 760 days.

(21) Appl. No.: 17/507,937

(22) Filed: Oct. 22, 2021

(65) Prior Publication Data
US 2022/0039893 A1    Feb. 10, 2022

Related U.S. Application Data

(62) Division of application No. 15/568,356, filed as application No. PCT/US2016/028575 on Apr. 21, 2016, now Pat. No. 11,185,380.
(Continued)

(51) Int. Cl.
*A61B 34/30*    (2016.01)
*A61B 34/00*    (2016.01)
(Continued)

(52) U.S. Cl.
CPC .............. *A61B 34/71* (2016.02); *A61B 34/30* (2016.02); *A61B 34/35* (2016.02); *B25J 9/1045* (2013.01); *A61B 2034/715* (2016.02)

(58) Field of Classification Search
CPC ......... A61B 34/71; A61B 34/30; A61B 34/35; A61B 2034/715; B25J 9/1045
See application file for complete search history.

(56) References Cited

U.S. PATENT DOCUMENTS 6,394,998 B1    5/2002   Wallace et al.
7,736,254 B2    6/2010   Schena
(Continued)

FOREIGN PATENT DOCUMENTS

EP    3168013 A1    5/2017
JP    2002200092 A    7/2002
(Continued)

OTHER PUBLICATIONS

Extended European Search Report for Application No. EP22157629.1, mailed on May 25, 2022, 10 pages.
(Continued)

*Primary Examiner* — Gary Jackson
*Assistant Examiner* — Skylar Lindsey Christianson
(74) *Attorney, Agent, or Firm* — JONES ROBB, PLLC

(57) ABSTRACT

A device to regulate tension of an actuation element for actuating movement of a surgical instrument includes an elastically deformable body configured to be coupled to the actuation element. The deformable body is configured to elastically deform in response to a state of slack occurring in the actuation element. As slack occurs in the actuation element, the deformable body is configured to divert a path of the actuation element to accommodate the slack so the path of the actuation element differs from an axis the actuation element follows prior to the actuation element developing slack. A force transmission mechanism for a teleoperated surgical instrument includes a chassis, an actuation input mechanism, an actuation element, and a tension
(Continued)

regulator coupled to the actuation element to compensate for slack of the actuation element.

20 Claims, 9 Drawing Sheets

Related U.S. Application Data

(60) Provisional application No. 62/151,138, filed on Apr. 22, 2015.

(51) Int. Cl.
    *A61B 34/35*     (2016.01)
    *B25J 9/10*     (2006.01)

(56) References Cited

U.S. PATENT DOCUMENTS

| | | | |
|---|---|---|---|
| 8,545,515 | B2 | 10/2013 | Prisco et al. |
| 8,852,208 | B2 | 10/2014 | Gomez et al. |
| 11,185,380 | B2 | 11/2021 | Burbank et al. |
| 11,234,784 | B2 | 2/2022 | Alden |
| 2001/0031983 | A1 | 10/2001 | Brock et al. |
| 2006/0084945 | A1 | 4/2006 | Moll et al. |
| 2011/0264018 | A1 | 10/2011 | Matjacic et al. |
| 2013/0325031 | A1 | 12/2013 | Schena et al. |
| 2013/0325033 | A1 | 12/2013 | Schena et al. |
| 2014/0128849 | A1 | 5/2014 | Au et al. |
| 2014/0257333 | A1 | 9/2014 | Blumenkranz |
| 2015/0257744 | A1 | 9/2015 | Alden et al. |
| 2017/0105805 | A1* | 4/2017 | Hasegawa .............. A61B 34/30 |
| 2018/0116741 | A1* | 5/2018 | Garcia Kilroy .. A61B 17/00234 |
| 2022/0110704 | A1 | 4/2022 | Alden |

FOREIGN PATENT DOCUMENTS

| | | | |
|---|---|---|---|
| JP | 2004176532 | A | 6/2004 |
| JP | 2010194102 | A | 9/2010 |
| WO | WO-2011143022 | A1 | 11/2011 |
| WO | WO-2013190475 | A2 | 12/2013 |
| WO | WO-2016006370 | A1 | 1/2016 |
| WO | WO-2016172299 | A1 | 10/2016 |

OTHER PUBLICATIONS

Openbuilds: "OpenBuilds Belt Tension—Torsion Spring," Oct. 1, 2013, XP055920841, Retrieved from the Internet: URL:https://www.youtube.com/watch?v=PO-OIJuC9UMt=32s, 2 pages.
Extended European Search Report for Application No. EP16783826.7, mailed on Nov. 16, 2018, 8 pages.
International Preliminary Report on Patentability for Application No. PCT/US2017/052638, mailed on Apr. 4, 2019, 13 pages.
International Search Report and Written Opinion for Application No. PCT/US2016/028575, mailed on Jul. 12, 2016, 10 pages.
International Search Report and Written Opinion for Application No. PCT/US2017/052638, mailed on Jan. 9, 2018, 19 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

TENSION REGULATOR FOR ACTUATION ELEMENTS, AND RELATED REMOTELY ACTUATED INSTRUMENTS, SYSTEMS, AND METHODS

RELATED APPLICATIONS

This application is a divisional of U.S. application Ser. No. 15/568,356, filed Oct. 20, 2017, which is a national stage application of International Application No. PCT/US2016/028575, filed Apr. 21, 2016, which claims priority to and the benefit of the filing date of U.S. Provisional Patent Application 62/151,138, filed Apr. 22, 2015, each of which is incorporated herein by reference in its entirety.

TECHNICAL FIELD

Aspects of the present disclosure relate to regulate tension in actuation elements, for example, via one or more devices used in a force transmission mechanism including such actuation elements. In particular, aspects of the present disclosure relate to surgical instruments that are actuatable through a force transmission mechanism including one or more such tension regulating mechanisms.

INTRODUCTION

Benefits of minimally invasive surgery are well known, and they include less patient trauma, less blood loss, and faster recovery times when compared to traditional, open incision surgery. In addition, the use of teleoperated surgical systems (e.g., robotic systems that provide telepresence), such as the da Vinci® Surgical System manufactured by Intuitive Surgical, Inc. of Sunnyvale, Calif. is known. Such teleoperated surgical systems may allow a surgeon to operate with intuitive control and with precision.

To perform actions directed by a surgeon, a surgical instrument may use a force transmission mechanism that receives drive inputs and transmits associated forces via actuation elements from a proximal end of the surgical instrument, along its shaft, to a distal portion of the surgical instrument. In some cases, the actuation elements include tension members, such as cables, wires, or the like. Slack that may develop in such actuation elements can affect the transmission of force along such actuation elements. In addition, slack can lead to misalignment and/or derailment of actuation elements, such as, for example, at capstans or pulleys. It is desirable, therefore, to provide ways to manage slack so as to minimize or prevent misalignment or derailment of actuation elements and/or to provide responsiveness of force transmission from the drive input at the force transmission mechanism to the ultimate actuation of a distal end portion of the surgical instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a device to regulate tension of an actuation element for actuating movement of a surgical instrument comprises an elastically deformable body configured to be coupled to the actuation element. The deformable body is configured to elastically deform in response to a state of slack occurring in the actuation element. As slack occurs in the actuation element, the deformable body is configured to divert a path of the actuation element to accommodate the slack so the path of the actuation element differs from an axis the actuation element follows prior to the actuation element developing slack.

In accordance with at least one exemplary embodiment, a force transmission mechanism for a teleoperated surgical instrument comprises a chassis, an actuation input mechanism mounted to the chassis, an actuation element, and a tension regulator. The actuation input mechanism is configured to receive forces from an actuation interface assembly of a teleoperated surgical system. The actuation element is configured to transmit force sufficient to actuate an end effector of the surgical instrument. The tension regulator is coupled to the actuation element to compensate for slack of the actuation element. As slack occurs in the actuation element, the tension regulator is configured to divert a path of the actuation element to accommodate the slack so the path of the actuation element differs from an axis the actuation element follows prior to the actuation element developing slack.

In accordance with at least one exemplary embodiment, a method of compensating for slack in an actuation element of a surgical instrument comprises coupling a tension regulator comprising an elastically deformable body to the actuation element, and compensating for slack developing in the actuation element by diverting a path of the actuation element so the path of the actuation element differs from an axis the actuation element follows prior to the actuation element developing slack.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
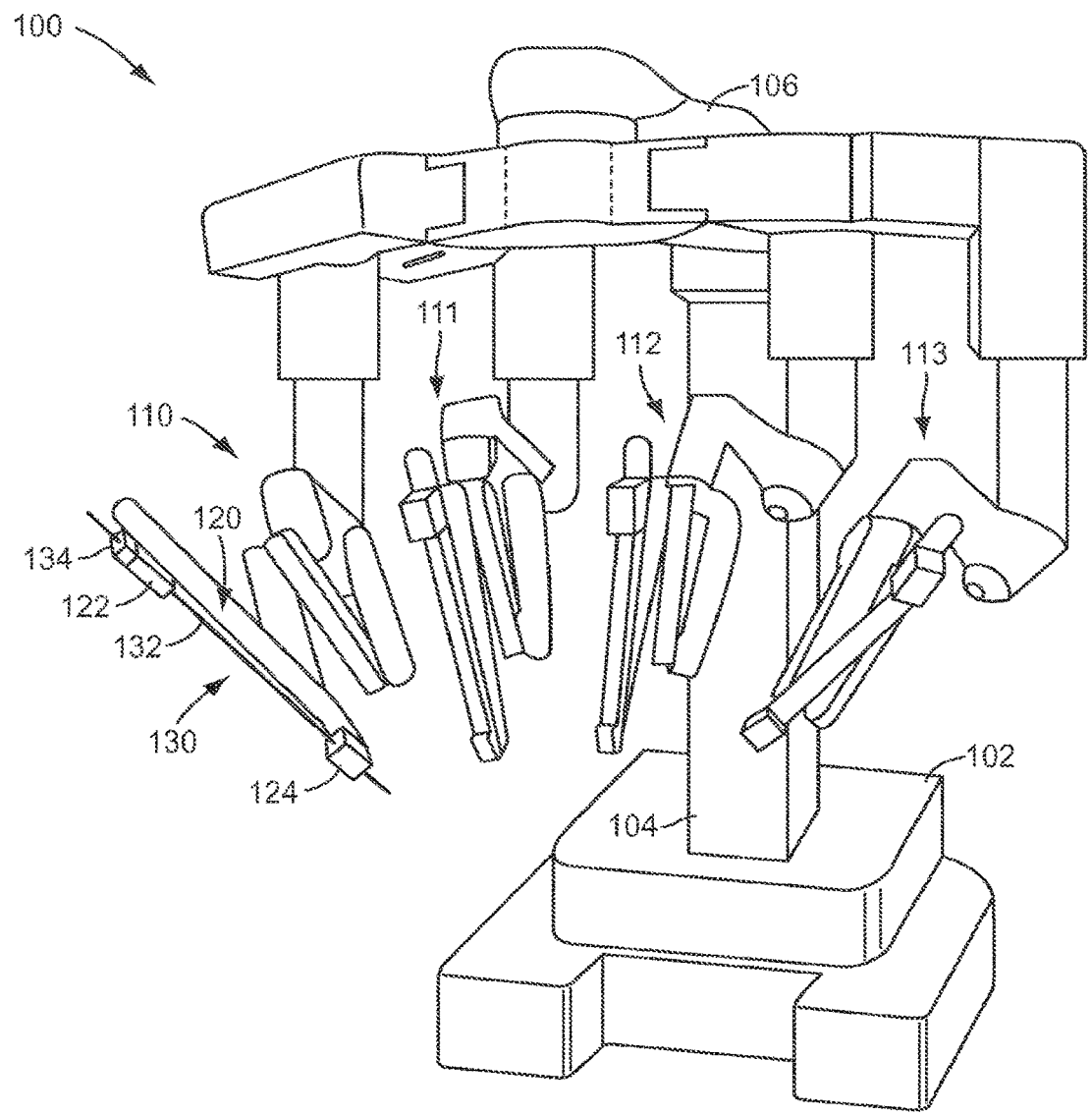
FIG. 1 shows a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates force transmission mechanisms that include tension regulators that compensate for slack in actuation elements. In various exemplary embodiments, the tension regulators may accommodate for slack in a passive manner. According to an exemplary embodiment, tension regulators may utilize potential energy to passively compensate for slack. For example, a tension regulator may passively compensate for slack by changing its configuration or shape (e.g., via elastic deformation) as slack develops. Tension regulators of the various exemplary embodiments described herein may permit tension in an actuation element to be maintained without automated controls or manual adjustments, thus providing an efficient and robust means of regulating tension of an actuation element. Therefore, as an actuation element changes over time and develops slack, the tension regulator may compensate for slack and substantially maintain a desired tension in actuation element, as will be discussed below.

According to an exemplary embodiment, an actuation element may follow a substantially straight path as it extends from a transmission mechanism and into the shaft of a surgical instrument. To transmit forces to effect motion of different portions of the surgical instrument, an actuation element is generally in a state of tension. As slack occurs in an actuation element, however, in accordance with various exemplary embodiments, a tension regulator coupled to the actuation element may accommodate the slack by diverting a portion of the actuation element away from an initial path of the actuation element in its taut state. For example, a tension regulator may form one or more bends in the actuation element such that a longitudinal axis of the actuation element is not straight at a location at which the tension regulator is disposed. A tension regulator may, therefore, accommodate slack by acting on the actuation element in the portion where slack occurs and exerting a force to maintain tension in that portion. As an actuation element loses tautness, a tension regulator coupled to the actuation element may pull an actuation element along a direction that is transverse (e.g., perpendicular) to an original path (e.g., straight path) of the portion of the actuation element, according to an exemplary embodiment. Diverting a portion of the length of the actuation element as the actuation element develops slack (i.e., loses tension), can serve to reestablish and maintain a tensioned, taut condition of the actuation element. According to an exemplary embodiment, a tension regulator may be configured to compensate (e.g., dynamically compensate) for varying amounts of slack (e.g., up to a maximum compensation amount the tension regulator is capable of), such as when the slack of an actuation element increases over time.

A tension regulator may be coupled to an actuation element along a portion of the actuation element that is disposed within a force transmission mechanism of a surgical instrument. In various exemplary embodiments, a tension regulator may be coupled to the actuation element such that the tension regulator moves with the actuation element when the actuation element is actuated according to an exemplary embodiment. In various exemplary embodiments, the tension regulator may be configured to float with respect to the force transmission mechanism (e.g., move with the actuation element relative to the force transmission mechanism), whereas in other exemplary embodiments, the tension regulator may be fixed to a force transmission mechanism, such as a chassis of a force transmission mechanism. According to an exemplary embodiment, a tension regulator may be coupled to one or more of a plurality of actuation elements connected to an actuation input mechanism. Although tension regulators may be coupled to regulate tension in a single actuation element, a tension regulator may be coupled so as to regulate tension in more than one actuation element simultaneously, according to an exemplary embodiment.

Various exemplary embodiments described herein contemplate tension regulators having a single piece (e.g., monolithic) construction. For example, a tension regulator may be a single piece of wire, a single piece of sheet metal, a single molded piece, a single band of elastic material, or other single piece constructions familiar to one of ordinary skill in the art. A portion of an actuation element extending through a tension regulator may be continuous length portion of the actuation element, according to an exemplary embodiment. In other words, the tension regulator may take up slack by acting on a portion of a length of the actuation element between ends of the actuation element, as opposed to, for example, acting on an end of the actuation element.

Referring now to FIG. 1, an exemplary embodiment of a patient side cart 100 of a teleoperated surgical system is shown. A teleoperated surgical system may further include a surgeon console (not shown) for receiving input from a user to control instruments mounted at patient side cart 100. A teleoperated surgical system also can include an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci® Surgical System, da Vinci® Si Surgical System, Single Site da Vinci® Surgical System, or a da Vinci® Xi Surgical System, available from Intuitive Surgical, Inc.

Patient side cart 100 may include a base 102, a main column 104, and a main boom 106 connected to main column 104. Patient side cart 100 may also include a plurality of manipulator arms 110, 111, 112, 113, which may each be connected to main boom 106. Manipulator arms 110, 111, 112, 113 may each include an instrument mount portion 120 to which an instrument 130 may be mounted, which is illustrated as being attached to manipulator arm 110. Portions of manipulator arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100, for example through drive interface devices and ultimately to the surgical instrument transmission mechanism, to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124, with a shaft 132 of instrument 130 extending through cannula mount 124 (and on to a surgery site during a surgical procedure) and a force transmission mechanism 134 of instrument 130 connecting with the actuation interface assembly 122, according to an exemplary embodiment. Cannula mount 124 may be configured to hold a cannula (not shown in FIG. 1) through which shaft 132 of instrument 130 may extend to a surgery site during a surgical procedure. Actuation interface assembly 122 may contain a variety of drive (e.g., input drive) and other mechanisms that are controlled to respond to input commands at the surgeon console and transmit forces to the force transmission mechanism 134 to actuate instrument 130, as those skilled in the art are familiar with, and thus can be broadly classified as a drive interface device. For instance, the input drives of actuation interface assembly 122 may directly engage with an interface structures (not shown) of force transmission mechanism 134 and transmit forces to force transmission mechanism 134, as will be discussed below.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
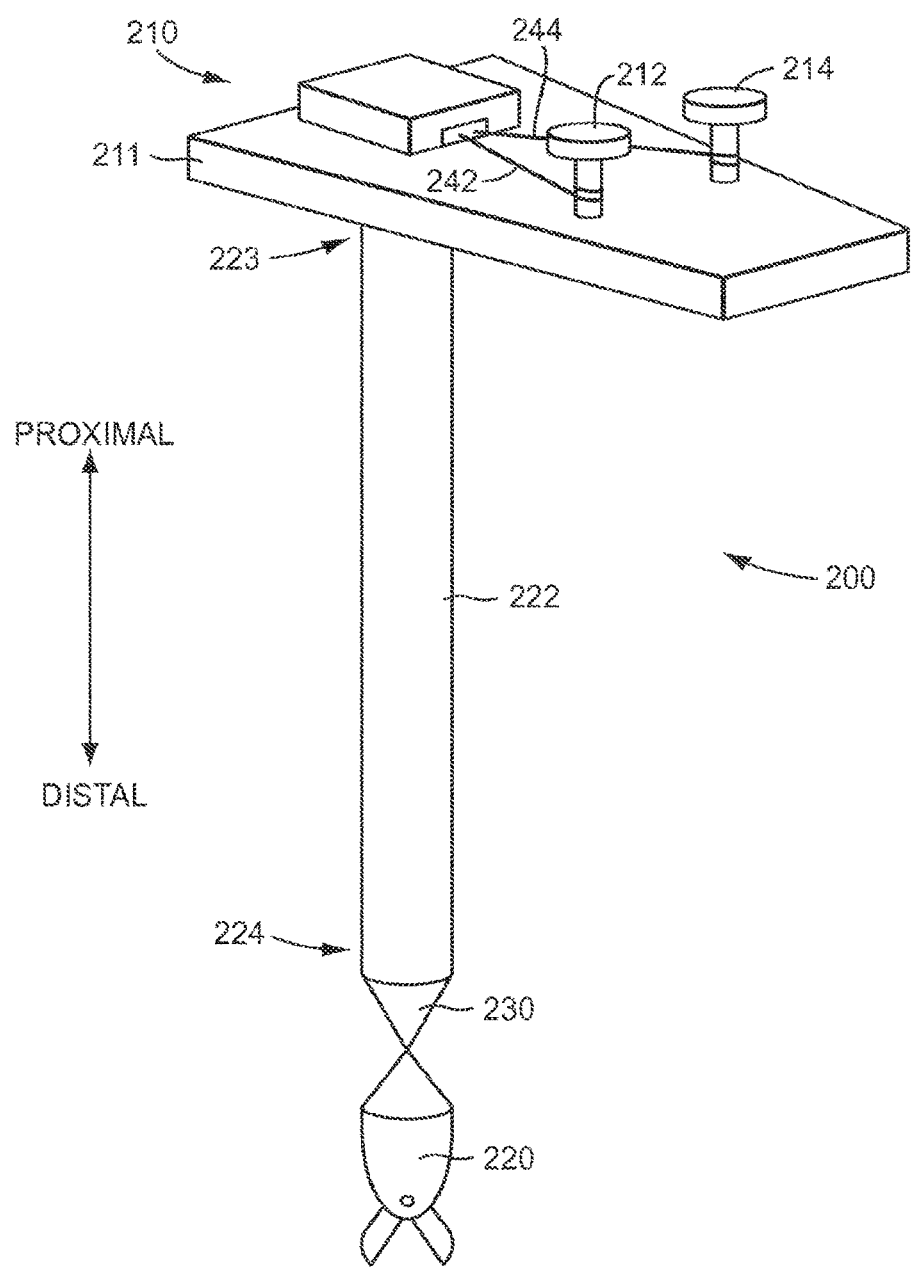
FIG. 2 shows a diagrammatic perspective view of a surgical instrument, according to an exemplary embodiment.

Turning to FIG. 2, a schematic side view of an exemplary embodiment of a surgical instrument 200 is shown. For instance, surgical instrument 200 may be used as instrument 130 with the patient side cart 100 of the exemplary embodiment of FIG. 1. Surgical instrument 200 may include a force transmission mechanism 210 (a chassis 211 for which is shown in the exemplary embodiment of FIG. 2, with a housing being removed from the illustration so as reveal components of the force transmission mechanism 210 within), a shaft 222 connected to force transmission mechanism 210 at a proximal end 223 of shaft 222, a wrist 230 connected to a distal end 224 of shaft 222, and an end effector 220 connected to wrist 230. Shaft 222 may be flexible or rigid. According to an exemplary embodiment, shaft 222 may have a diameter ranging from about 3 mm to about 15 mm. According to another exemplary embodiment, the diameter of shaft 222 may range, for example, from about 5 mm to about 8 mm. End effector 220 may comprise, for example, forceps, a needle driver for suturing, cutting devices, dissecting devices, clip appliers, and other end effector configurations for performing various surgical procedures.

Surgical instrument 200 may include one or more members to translate force between force transmission mechanism 210 and end effector 220 and/or between force transmission mechanism 210 and wrist 230. For example, actuation elements 242, 244 may connect force transmission mechanism 210 to end effector 220 to provide actuation forces to end effector 220, such as by extending through an interior of shaft 222. By utilizing actuation elements 242, 244, force transmission mechanism 210 may actuate end effector 220 to control, for example, a jaw of end effector 220 (or other moveable part of end effector 220). In another example, actuation elements 242, 244 may be utilized to actuate wrist 230 in one or more degrees of freedom (e.g. pitch and/or yaw). Actuation elements 242, 244 may be in the form of tension members, such as when force transmission mechanism 210 is a pull-pull mechanism, as described in U.S. Pat. No. 8,545,515, which is hereby incorporated by reference in its entirety.

Force transmission mechanism 210 may include one or more components to engage with a patient side cart 100 of a teleoperated surgical system to translate a force provided by patient side cart to surgical instrument 200. For example, force transmission mechanism 210 may connect with the actuation interface assembly 122 of the patient side cart 100 of the exemplary embodiment of FIG. 1 so actuation interface assembly 122 may transmit forces to force transmission mechanism 210 to actuate instrument 200. According to an exemplary embodiment, force transmission mechanism 210 may include one or more driven actuation input mechanisms 212, 214 that engage (e.g., via a distal end of force transmission mechanism 210) with a manipulator of a patient side cart, such as actuation interface assembly 122 of patient side cart 100.

According to an exemplary embodiment, actuation input mechanisms 212, 214 may interact with a manipulator of a patient side cart, such as actuation interface assembly 122 of patient side cart 100, via a sterile adapter (not shown), as will be described below. One exemplary type of actuation input mechanism that can be used in force transmission mechanism 210 is a pull-pull mechanism, exemplary embodiments of which are described in U.S. Pat. No. 8,545,515, which is hereby incorporated by reference in its entirety. According to an exemplary embodiment, force transmission mechanism 210 may utilize a pull-pull mechanism, actuation elements 242, 244 may be tension members, and driven actuation input mechanisms 212, 214 may be capstans that are rotationally driven by actuation interface assembly 122 to tension actuation elements 242, 244 to actuate instrument. Thus, driven actuation input mechanisms 212, 214 utilize actuation forces from an actuation interface assembly to actuate instrument 200. Force transmission mechanism 210 may include other components in addition to or in lieu of capstans to actuate various other functionalities of a surgical instrument, as those having ordinary skill in the art are familiar with. Such components include, but art no limited to, gears, clutches, pulleys, linkages, and other mechanisms to convert input force and/or motion into a desired output force and/or motion. Further, force transmission mechanism 210 may include other numbers of actuation input mechanisms 212, 214 than shown in the exemplary embodiment of FIG. 2, such as, for example, one, three, four, five, six, seven, eight or more actuation input mechanisms. For example, any number of actuation input mechanisms 212, 214 may be used, depending on the nature of a surgical instrument and depending upon the degrees of operational freedom of such an instrument.

The force transmission mechanism of FIG. 2 provides an accurate conversion of rotational movement to translation movement of an actuation element for a surgical instrument of a teleoperated surgical system. However, actuation elements of a force transmission mechanism can experience a change in shape. For example, actuation element 242 of the exemplary embodiment of FIG. 2, which may be a tension member, may deform, such as by stretching and increasing in length in proportion to a load delivered. As a result, actuation element 242 may develop slack. Actuation element 244 may move in coordination with actuation element 242 if both are coupled to a movement of the wrist 230 or end effector 220. With such coordinated movement, actuation element 244 also may develop slack. Conversely, actuation element 242 could be in tension, with actuation element 244 having slack. Further, when actuation elements 242, 244 are in a state of slack, the precision of force transmission mechanism 210 to actuate instrument 200, such as end effector 220 or wrist 230, may diminish. For instance, rotation of driven actuation input mechanisms 212, 214 may need to be rotated to remove slack from actuation elements 242, 244 in order to place the actuation elements 242, 244 in a taut state in which they can actuate instrument 200. In addition, driven actuation input mechanisms 212, 214 may include a groove (not shown) in which the actuation elements 242, 244 normally lie during use of force transmission mechanism 210. Slack in actuation elements 242, 244 could become significant enough that actuation elements 242, 244 move out of the groove, which can also affect the actuation of instrument 200. Therefore, further improvements can be made with surgical instrument components to compensate for changes in actuation elements, such as by using tension regulation devices that utilize the limited space within a surgical instrument in a more efficient way.

Figure 3:
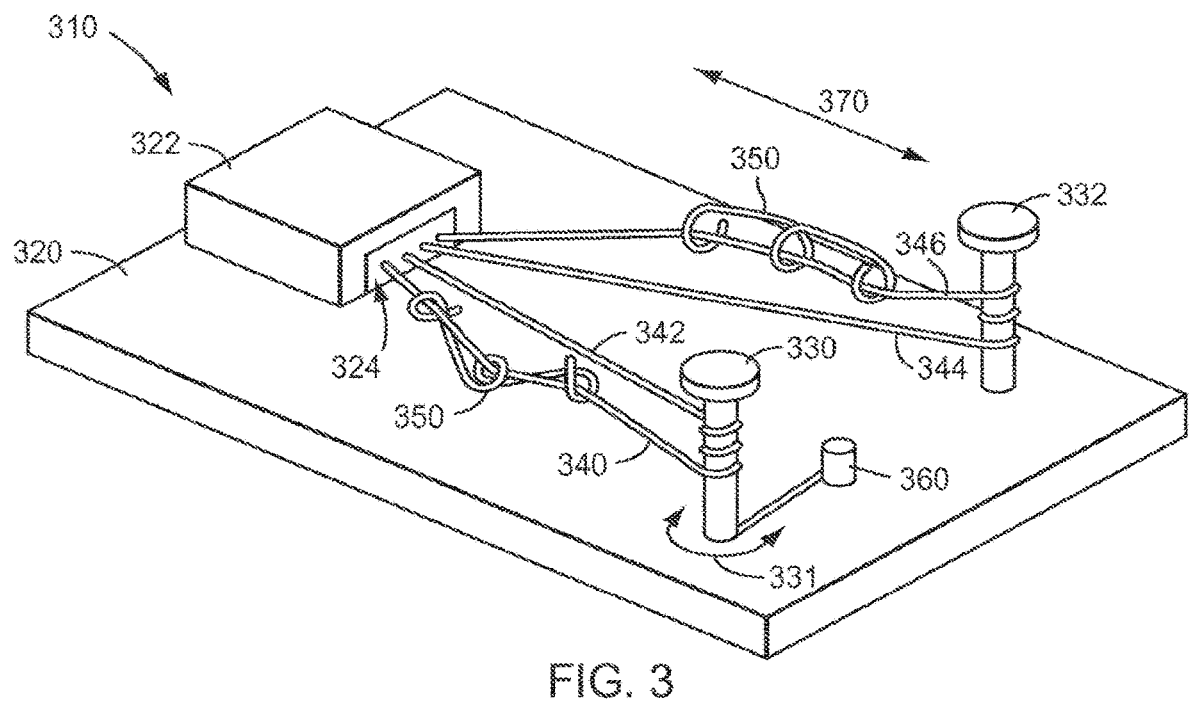
FIG. 3 is a perspective view of an interior portion and chassis of a force transmission mechanism, according to an exemplary embodiment.

Turning to FIG. 3, an interior portion of a force transmission mechanism 310 is shown, according to an exemplary embodiment. Force transmission mechanism 310 may comprise a chassis 320 and a housing (not illustrated to reveal components of force transmission mechanism 310 within). Force transmission mechanism 310 may be used as transmission mechanism 134 of instrument 130 of the exemplary embodiment of FIG. 1. According to an exemplary embodiment, force transmission mechanism 310 may comprise other components, such as, for example, a roll gear (not shown) to engage a proximal portion of a shaft (not shown) of an instrument and roll the shaft, such as shaft 222 of instrument 200 in the exemplary embodiment of FIG. 2, flux conduits to deliver flux (e.g., electrical energy, fluids, suction, light, etc.) to an end effector of an instrument, and other components familiar to one of ordinary skill in the art.

Force transmission mechanism 310 may comprise one or more actuation input mechanisms 330, 332, as shown in the exemplary embodiment of FIG. 3. In an exemplary, non-limiting embodiment, actuation input mechanisms 330, 332 may be capstans, as discussed above with regard to actuation input mechanisms 212, 214 of the exemplary embodiment of FIG. 2, although various other actuation input mechanism configurations may be used without departing from the scope of the present disclosure. Actuation elements may be respectively coupled to driven actuation input mechanisms 330, 332. For example, actuation elements 340, 342 may be coupled to actuation input mechanism 330 and actuation elements 344, 346 may be coupled to actuation input mechanism 332, as shown in the exemplary embodiment of FIG. 3. According to an exemplary embodiment, actuation elements 340, 342, 344, 346 may be tension members, such as cables, as described in U.S. Pat. No. 8,545,515, issued Oct. 1, 2013, which is hereby incorporated by reference in its entirety. According to an exemplary embodiment, a pull-pull mechanism may include two tension members, with one tension member pulled to actuate an end effector or wrist in one direction and the other tension member pulled to actuate the end effector or wrist in another direction. According to another exemplary embodiment, a pull-pull mechanism may include a single tension element (e.g., a single tension element wrapped about a capstan or other actuator), with one portion of the tension element pulled to actuate an end effector or wrist in one direction and another portion of the tension member pulled to actuate the end effector or wrist in another direction. Chassis 320 of force transmission mechanism 310 may further comprise a chassis portion 322 that defines an exit aperture 324 into which actuation elements 340, 342, 344, 346 extend so actuation elements 340, 342, 344, 346 may be routed through a shaft (e.g., shaft 222 in FIG. 2) to a distal portion of an instrument, according to an exemplary embodiment.

The actuation elements connected to a driven actuation input mechanism may be formed by a single actuation element, according to an exemplary embodiment. Thus, actuation elements 340, 342 connected to actuation input mechanism 330 may be formed by a single actuation element, with actuation elements 340, 342 defined by two potions of the single actuation element that extend between force transmission mechanism 310 and a distal portion of an instrument. For example, actuation elements 340, 342 may be portions of a single actuation element (e.g., cable) that loops about actuation input mechanism 330 at one end in force transmission mechanism, extends from force transmission mechanism 310 through the shaft of an instrument (e.g., shaft 222 in FIG. 2), to a distal portion of an instrument (e.g., wrist 230 or end effector 220 in FIG. 2) to actuate instrument when actuation input mechanism 330 is driven. Thus, when actuation input mechanism 330 is driven, such as by being rotated along the directions indicated by arrows 331 in the exemplary embodiment of FIG. 3, one of the portions of the single actuation element (e.g., one of actuation elements 340, 342) is paid out from actuation input mechanism 330 while the other portion of the single actuation element (e.g., the other of actuation elements 340, 342) is taken up (e.g., wound upon) actuation input mechanism 330. Actuation elements 344, 346 connected to actuation input mechanism 332 may be similarly arranged.

According to another exemplary embodiment, actuation elements 340, 342 may be two separate actuation elements. For example, a first end of each of actuation elements 340, 342 may be connected to actuation input mechanism 330 and a second end of each of actuation elements 340, 342 may be connected to a distal portion of an instrument (e.g., wrist 230 or end effector 220). Actuation elements 344, 346 connected to actuation input mechanism 332 may be arranged as two separate actuation elements, according to an exemplary embodiment. Thus, actuation elements (e.g., actuation elements 340, 342 in FIG. 3) connected to an actuation input mechanism (e.g., actuation input mechanism 330 in FIG. 3) may be two portions of a single actuation element or may be defined by two actuation elements.

According to an exemplary embodiment, tension regulators of the various exemplary embodiments described herein may be coupled to at least one actuation element of a force transmission mechanism either before or after the force transmission mechanism has been assembled. For example, a tension regulator may be coupled to an actuation element after the actuation element has been connected to a wrist or end effector of an instrument (e.g., 230 or 220 in FIG. 2) and connected to an actuation input mechanism (e.g., 330 or 332 in FIG. 3). According to another exemplary embodiment, a tension regulator may be coupled to an actuation element and then the actuation element may be connected to a wrist or end effector of an instrument (e.g., 230 or 220 in FIG. 2) and connected to an actuation input mechanism (e.g., 330 or 332 in FIG. 3).

As shown in the exemplary embodiment of FIG. 3, tension regulator 350 may be coupled to one or more actuation elements of force transmission mechanism 310 and be configured to passively compensate for slack in the one or more actuation elements. In various exemplary embodiments, tension regulator 350 may be uncoupled to chassis 320 of force transmission mechanism 310 and thus may translate freely with an actuation element.

Because of the way in which tension regulator 350 is coupled to an actuation element (e.g., one of actuation elements 340, 342, 344, 346), as the actuation element is wound upon or paid out from a respective actuation input mechanism (e.g., actuation input mechanism 330 or 332), such as along the directions indicated by arrows 370 in the exemplary embodiment of FIG. 3, tension regulator 350 also moves along the directions indicated by arrows 370 relative to chassis 320. One consideration for such a configuration in which tension regulator 350 is coupled to an actuation element is that as the actuation element moves back and forth between an actuation input mechanism and aperture 324, tension regulator 350 could impact the actuation input mechanism, or tension regulator 350 could impact chassis portion 322 defining aperture 324. Due to the size of force transmission mechanism 310 and the distance an actuation element travels between aperture 324 and an actuation input mechanism, a small space is provided for a tension regulator 350 to travel when coupled to an actuation element. In view of this, a tension regulator 350 configured to be coupled to an actuation element may be designed to compensate for slack of the actuation element but also have a size small enough to minimize or eliminate impacts between the tension regulator 350 and chassis portion 322 or an actuation input mechanism.

In various exemplary embodiments, a tension regulator may be coupled to only one of the actuation elements connected to an actuation input mechanism (e.g., when actuation elements 340, 342 in FIG. 3 are defined by two actuation elements) or coupled to only one portion of a single actuation element that extends between a force transmission mechanism and a distal portion of an instrument (e.g., when actuation elements 340, 342 in FIG. 3 are portions of a single actuation element). However, the various exemplary embodiments described herein are not limited to such configurations and may instead have tension regulators coupled to more than one actuation element of a given actuation input mechanism. According to an exemplary embodiment, a tension regulator may be coupled to each actuation element for an actuation input mechanism. Coupling of tension regulators to actuation elements may be based upon, for example, a function of a component being actuated by the actuation elements, according to an exemplary embodiment.

Figure 4:
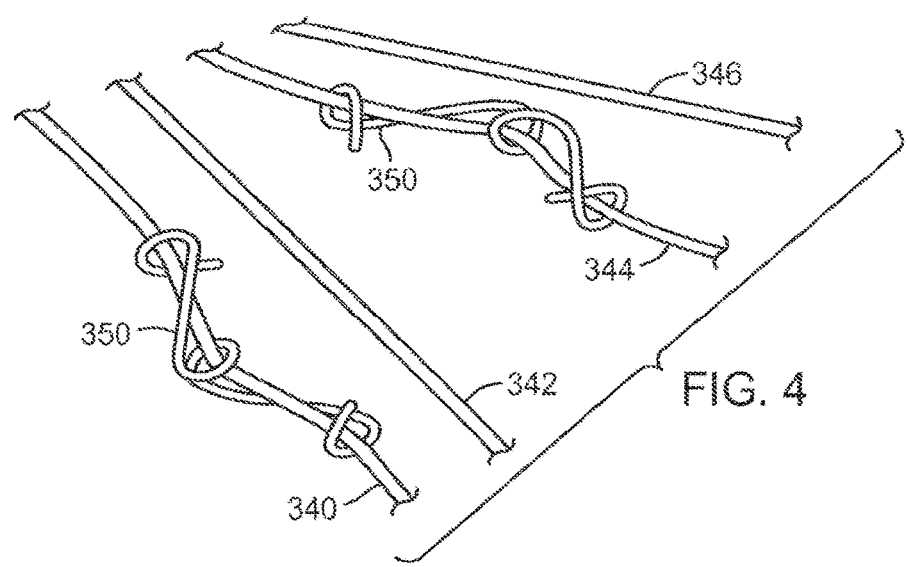
FIG. 4 is a partial, perspective view of actuation elements and tension regulators of FIG. 3.

As shown in the exemplary embodiment of FIG. 4, which is a partial view of actuation elements 340, 342, 344, 346 of the exemplary embodiment of FIG. 3, a tension regulator 350 may be coupled to actuation element 340 but not to actuation element 342. Similarly, a tension regulator 350 is coupled to actuation element 344. In other words, actuation elements 342 and 346 may lack tension regulators 350, as shown in FIGS. 3 and 4.

In a situation where slack is present in both paired actuation elements (e.g., actuation elements 340 and 342 or actuation elements 344 and 346), precise control of end effector elements can be improved by selectively accumulating the entire slack onto only one actuation element of a pair of actuation elements. For example, all slack may be accumulated with a single tension regulator 350 coupled to one of actuation elements 340 and 342 or to one of actuation elements 344 and 346. Thus, all slack in paired actuation elements 340, 342 or in paired actuation elements 344, 346 accumulates in a tension regulator 350 coupled to one of the actuation elements (e.g., one of actuation elements 340, 342) of the respective pairing, while the other actuation element of the pairing (e.g., the other of actuation elements 340, 342) is drawn taut due to the removal of slack from the pair of actuation elements via the tension regulator 350. Because the other actuation element is taught and substantially straight, the length of the other actuation element is substantially known, which facilitates precise control of an element actuated by the actuation element.

By way of example, when tension regulator 350 is coupled to actuation element 340 and not to actuation element 342, the tension regulator 350 accumulates all slack of the paired actuation elements 340 and 342. In this way, actuation element 342 becomes taught, as indicated in FIG. 4, and the length of actuation element 342 is substantially known. Actuation input mechanism 330 may be rotated (e.g., along directions 330) by an amount corresponding to the length of actuation element 342 in order to precisely control an end effector element actuated by actuation element 342. Conversely, when the length of actuation element 342 is not substantially known, such as due to slack in actuation element 342, rotation of actuation input mechanism 330 does not necessarily provide precise control of an end effector element because the rotation of actuation input mechanism 330 is no longer matched to the length of actuation element. In other words, an amount of rotation of actuation input mechanism 330 no longer corresponds to a particular amount of paying out or winding up of actuation element 342 because slack is present in actuation element 342.

According to various exemplary embodiments, a tension regulator 350 may be selectively coupled to an actuation element depending upon a function of the actuation element. Coupling a tension regulator 350 to an actuation element (e.g., actuation element 340) may result in the removal of slack between a pair of actuation elements (e.g., actuation elements 340, 342) and cause an actuation element of the pair that is not coupled to a tension regulator (e.g., actuation element 342) to become taut and straight, as indicated in FIG. 4, while the other actuation element to which the tension regulator 350 is coupled (e.g., actuation element 340), is no longer straight in view of the function of the tension regulator 350 accumulating the slack. Because one actuation element (e.g., actuation element 342) is taut, its length is substantially known, which facilitates precise functioning of the actuation element, such as to operate an end effector by moving the actuation element an amount corresponding to its length. Conversely, the other actuation element (e.g., actuation element 340) is not straight and therefore it may be more difficult to use the other actuation element in a precise manner because of its length not being precisely known. In view of these considerations, one may select which actuation element, of a pair of actuation elements, to couple a tension regulator to based upon the function of the actuation element and how much precision is desirable when using the function of the actuation element.

For example, tension regulators 350 in FIGS. 3 and 4 may be coupled to actuation elements 340 and 344 that are pulled to actuate an end effector (e.g., end effector 220 in FIG. 2) to an open position, while not being coupled to actuation elements 342, 346 that are pulled to actuate the end effector to a closed position. Greater precision may be desirable, for example, for closing an end effector than opening the end effector, with coupling of the tension regulators 350 being selected in view of this consideration. In such an arrangement, slack is minimized or eliminated by coupling tension regulators 350 to actuation elements 340 and 344 because actuating the end effector to an open position may be accomplished with less precision and force than actuating the end effector to a closed position. Conversely, actuation elements 342 and 346 may lack tension regulators 350 but are taut due to the removal of slack via the tension regulators 350 coupled to actuation elements 340, 344. Thus, the end effector may be effectively closed in an accurate manner with a desired amount of force by tensioning actuation elements 342, 346.

Figure 5:
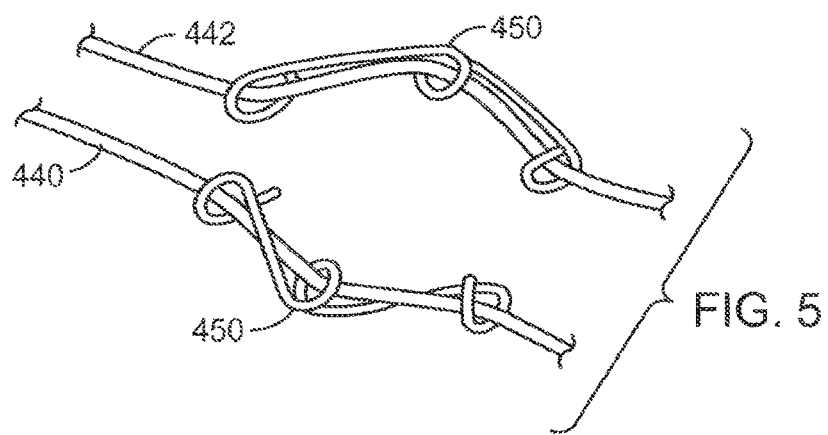
FIG. 5 is a partial view of actuation elements each including a tension regulator, according to an exemplary embodiment.

According to another exemplary embodiment, a tension regulator may be coupled to each actuation element for an actuation input mechanism, as depicted in the exemplary embodiment of FIG. 5. FIG. 5 is a partial view of actuation elements 440 and 442 connected to a single actuation input mechanism (not shown), such as actuation input mechanism 330 or 332 in the exemplary embodiment of FIG. 3. A tension regulator 450 is coupled to each of actuation elements 440 and 442, as shown in FIG. 5.

As shown in the exemplary embodiments of FIGS. 3-5, a single tension regulator may be coupled to an actuation element. However, the various exemplary embodiments described herein are not limited to a single actuation element being coupled to a particular actuation element. According to an exemplary embodiment, more than one tension regulator may be coupled to a particular actuation element. For example, two, three, or more tension regulators may be coupled to a particular actuation element.

Figure 6:
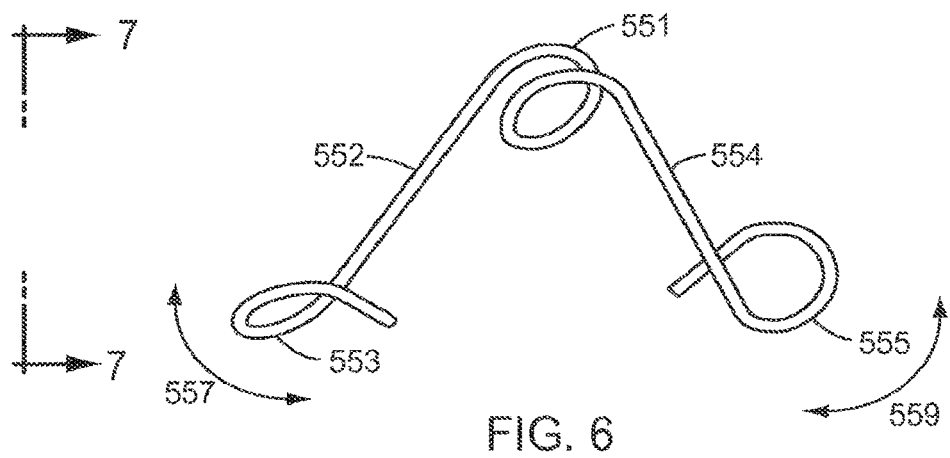
FIG. 6 is a plan view of a tension regulator, according to an exemplary embodiment.
Figure 7:
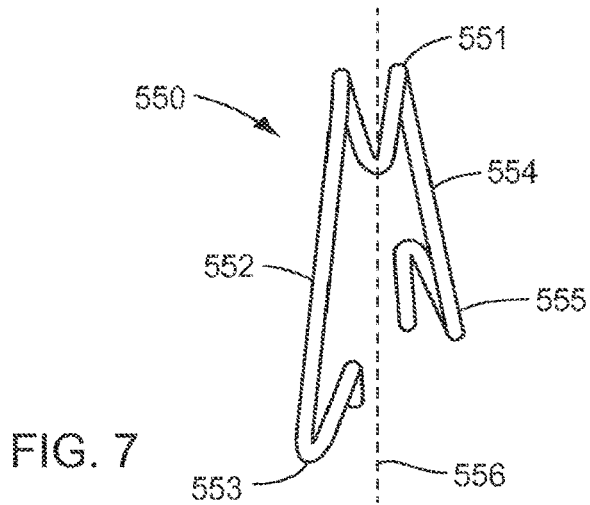
FIG. 7 is a side view taken from the view 7-7 in FIG. 6.

Turning to FIG. 6, an exemplary embodiment of a tension regulator 550 is shown. Tension regulator 550 may be coupled to an actuation element, such as, for example, any of actuation elements 340, 342, 344, 346 of the exemplary embodiment of FIG. 3. Tension regulator 550 may be made of, for example, stainless steel or other surgical instrument materials familiar to one of ordinary skill in the art. Tension regulator 550 may comprise a first leg 552 and a second leg 554 connected by a main loop 551. First leg 552 may be configured to move (e.g., in a rotational manner) relative to main loop 551, such as about the directions indicated by arrows 557 in the exemplary embodiment of FIG. 6. Second leg 554 also may be configured to move (e.g., in a rotational manner) relative to main loop 551, such as about the directions indicated by arrows 559 in the exemplary embodiment of FIG. 6. According to an exemplary embodiment, movement of legs 552, 554 may be accomplished via, for example, elastic deformation of tension regulator 550.

Tension regulator 550 may further comprise end loops 553, 555 at each end of first and second legs 552, 554, as shown in FIG. 6. Loops 551, 553, 555 may function to couple tension regulator 550 to an actuation element. For example, an actuation element (not shown) may pass through each of loops 551, 553, 555 so tension regulator 550 is coupled to the actuation element. The loop configuration and illustrated in FIGS. 6-10 is intended to be exemplary and illustrative only, and it should be appreciated that various modifications can be made without departing from the scope of the present disclosure and claims. For example, the direction (helical direction), pitch, and/or diameter may be modified, for example, to minimize any localized stress risers in the actuation element. The loop structures in the tension regulator of FIGS. 6-10 also may enable the tension regulator to be coupled to an actuation element already installed in a force transmission mechanism for an instrument.

The rotation of the legs 552 and 554 about the main loop 551 transitions the tension regulator 550 between a configuration in which the tension regulator is approximately straight and a configuration in which the tension regulator is bent with a reduced angle (e.g., one or more acute angles or curves in the tension regulator) between the legs 552 and 554, according to an exemplary embodiment. According to an exemplary embodiment, bending of legs 552, 554, such as relative to main loop 551, may be accomplished via elastic deformation of tension regulator 550. For example, the material from which the tension regulator 550 is made permits an elastic deformation of the tension regulator between the approximately straight and bent configurations, with the bent configuration being the state into which the tension regulator is biased (e.g., the low energy state of the tension regulator). That is, absent a force acting in a manner to straighten the tension regulator 550, the tension regulator 550 is naturally in the bent configuration depicted in FIG. 6. According to an exemplary embodiment, tension regulator 550 may have a configuration intermediate the approximately straight configuration and the bent configuration depicted in FIG. 6, depending upon the amount of force applied to tension regulator 550 by an actuation element the tension regulator 550 is coupled to.

According to an exemplary embodiment, tension regulator 550 may be configured to divert an actuation element from a substantially straight path along a portion of its length as tension regulator 550 transitions from the approximately straight configuration, such as when the actuation element lacks slack, to the bent configuration of FIG. 6 as the actuation element develops slack. Tension regulator 550 may transition from the approximately straight configuration to the bent configuration via elastic deformation, which results in a dynamic change in the energy state of the tension regulator 550 (e.g., from a high energy state in its approximately straight configuration to a lower state in the bent configuration). Thus, tension regulator 550 may passively compensate for an increase in slack in actuation element.

Figure 8:
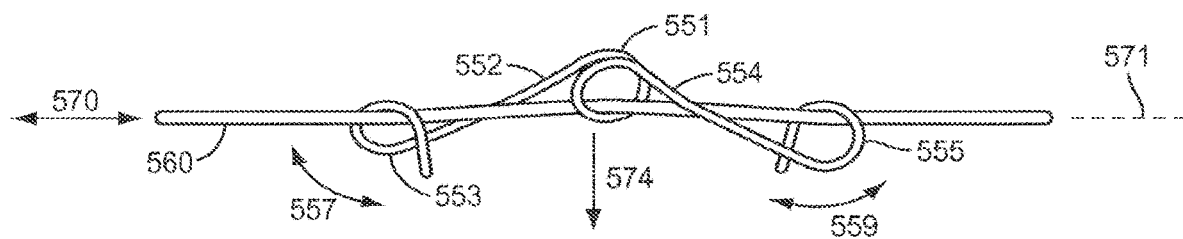
FIG. 8 depicts the tension regulator of FIG. 6 coupled to an actuation element in a taut state, according to an exemplary embodiment.

Use and operation of tension regulator 550 will now be described with regard to FIGS. 8-10, according to an exemplary embodiment. FIG. 8 depicts tension regulator 550, as described above with regard to FIGS. 6 and 7, coupled to an actuation element 560. In particular, actuation element 560 may be routed through loops 551, 553, 555 of tension regulator 550 so tension regulator 550 is fastened to actuation element 560. As a result, a portion of actuation element 560 may extend through tension regulator 550 in a continuous, uninterrupted manner. In other words, there is no need to attach tension regulator 550 to an end of actuation element 560, or to attach tension regulator 550 to separate ends of actuation element (e.g., with the tension regulator connecting the separate ends of the actuation element). Further, if actuation element 560 is pulled along the directions indicated by arrows 570 in FIG. 8, tension regulator 550 moves with actuation element 560, as described above with regard to the exemplary embodiment of FIG. 3. When a large amount of motion of actuation element 560 occurs, such that loops 553 or 555 encounter chassis portion 327 or capstan 330 of FIG. 3, for example, tension regulator 550 may slidingly adjust to a new position on actuation element 560 rather than limit travel of actuation element 560. In some embodiments, tension regulators may thus be relatively simply coupled to an actuation element already in an assembled state with the force transmission housing components by configuring tension members to be able to attach along a continuous length of the actuation element, as further described with respect to some exemplary embodiments below.

In the exemplary embodiment of FIG. 8, actuation element 560 is taut, substantially straight, and essentially lacks slack (e.g., prior to developing slack). Due to its coupling with tension regulator 550, actuation element 560 applies a force to tension regulator 550, such as by extending actuation element 560 through loops 551, 553, 555. This causes first leg 552 and second leg 554 be pulled away from each other (e.g., via elastically deformation) in directions 557 and 559, such as relative to main loop 551. As a result, tension regulator 550 has an increased amount of potential energy due to its substantially straightened, elongated configuration shown in FIG. 8, relative to when tension regulator 550 is not bent by actuation element 560. Because actuation element 560 extends through end loops 553, 555 and also main loop 551, and because actuation element 560 is taut and lacks slack in the exemplary embodiment of FIG. 8, actuation element 560 pulls legs 552, 554 and also pulls main loop 551, such as along direction 574 relative to a straight axis 571 of actuation element 560 when actuation element is in the state shown in FIG. 8. According to an exemplary embodiment, axis 571 may represent a path actuation element 560 follows when actuation element 560 is taut, substantially straight, and essentially lacks slack (e.g., prior to developing slack), as depicted in FIG. 8.

Over time, actuation element 560 may develop slack, such as, for example, due to deformation and elongation of actuation element 560. However, tension regulator 550 may compensate for the slack as the slack develops in actuation element 560. Turning to FIG. 9, tension regulator 550 and actuation element 560 are shown in state in which actuation element 560 has developed slack relative to the initial non-slack state shown in FIG. 8. As slack develops, actuation element 560 becomes less taut and applies less force to tension regulator 550. This results in tension regulator 550 relaxing to a degree and becoming less elastically deformed relative to the state shown in FIG. 8. For example, first leg 552 may bend relative to main loop 551 in the direction indicated by arrow 557 in FIG. 9 and second leg 554 may bend relative to main loop 551 in the direction indicated by arrow 559 in FIG. 9. First leg 552 and second leg 554 may bend until the slack has been removed and actuation element 560 is once again taut, as shown in FIG. 9.

Figure 9:
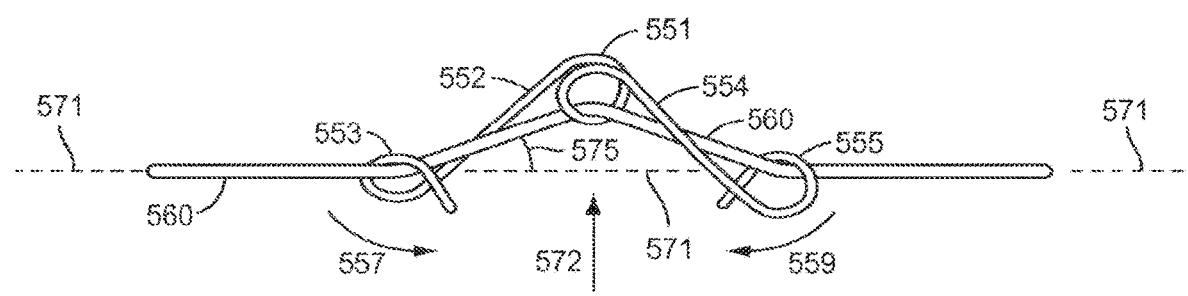
FIG. 9 depicts the tension regulator and actuation element of FIG. 8 in a slack state.
Figure 10:
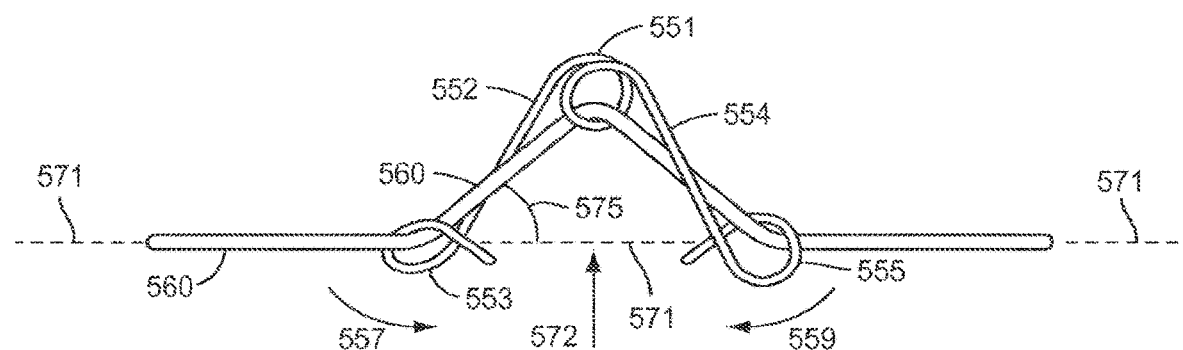
FIG. 10 depicts the tension regulator and actuation element of FIG. 9 another slack state.

According to an exemplary embodiment, tension regulator 550 may pull actuation element 560 along a direction indicated by arrows 572 in FIG. 9, which is substantially perpendicular to the axis 571 of actuation element 560 as the actuation element 560 develops slack. For example, main loop 551 may move along direction 572 in FIG. 9 and pull actuation element 560 locally relative to the axis 571 of actuation element 560 when actuation element is taut and substantially straight, as depicted in FIG. 8. As a result, some of the potential energy due to the deformation of tension regulator 550 (e.g., when the actuation element 560 is in a taut state and acting on the tension regulator 550) may be used to compensate for, and remove, slack from actuation element 560 so actuation element 560 may remain substantially taut and be used to actuate a surgical instrument. Thus, tension regulator 550 may compensate for slack in actuation element 560 via a dynamic change in the potential energy of tension regulator 550.

As shown in the exemplary embodiment of FIG. 8, actuation element 560 may be substantially straight when actuation element lacks slack. For example, actuation element 560 may extend along a substantially straight path when actuation element 560 is taut and substantially straight, such as along axis 571 depicted in FIG. 8. As actuation element 560 develops slack, tension regulator 550 may compensate for the slack by diverting actuation element 560 from the straight path along axis 571. As shown in FIG. 9, the portion of actuation element 560 extending through tension regulator 550 follows a path that diverges from the path extending along (e.g., is substantially coaxial to) longitudinal axis 571. For example, when actuation element 560 has developed slack, the portion of actuation element 560 extending through tension regulator 550 may follow a path through tension regulator 550 that has a non-zero angle 575 relative to axis 571, as shown in the exemplary embodiment of FIG. 9. Angle 575, which may depend upon the amount of tension of actuation element 560, may vary between, for example, about 5 degrees to about 80 degrees when actuation element 560 develops slack. According to another exemplary embodiment, tension regulator 550 may divert actuation element 560 along a path having an angle 575 of, for example, about 5 degrees to about 30 degrees when actuation element 560 develops slack.

According to an exemplary embodiment, if actuation element 560 develops slack, such as due to elongation of another actuation element that actuation element 560 is paired with or via an increase in the length of actuation element 560, such as via stretching of actuation element 560 along axis 571, tension regulator 550 may accommodate the slack in actuation element 560 by increasing the path length of the actuation element 560 in a direction differing from the path along (e.g., substantially coaxial to) axis 571 of actuation element 560 when actuation element 560 is taut and substantially straight, as depicted in FIG. 8. For example, tension regulator 550 may accommodate an increase in length of actuation element 560 by pulling actuation element along a direction 572 that is substantially transverse (e.g., perpendicular) to the longitudinal axis 571 of actuation element 560. As a result, the portion of actuation element 560 extending through tension regulator 550 may follow a path having an angle 575 relative to axis 571 of actuation element 560 when actuation element 560 is taut and substantially straight, as depicted in FIG. 8.

Tension regulator 550 may be configured to compensate for varying amounts of slack in actuation element 560. For example, the slack in actuation element 560 may further increase from the state shown in FIG. 9 to the exemplary embodiment shown in FIG. 10. As a result, tension regulator 550 may relax further and become less elastically deformed relative to the state shown in FIG. 9, so a change in potential energy of tension regulator 550 due to its deformation may be used to dynamically compensate for, and remove, the slack from actuation element 560. For example, first leg 552 and second leg 554 may further bend along their respective directions with regard to main loop 551, with main loop 551 moving further along direction 572 with regard to axis 571. Thus, tension regulator 550 may pull actuation element 560 further along direction 572 and angle 575 for the path of the portion of actuation element 560 extending through tension regulator 550 may increase as the amount of slack increases. As a result, even as the slack of actuation element 560 increases, tension regulator 550 may continue to compensate for the slack and keep actuation element 560 substantially taut.

Tension regulators of the exemplary embodiments described herein may have a maximum slack compensation amount. According to an exemplary embodiment, the maximum slack compensation amount may correspond to the amount of elastic deformation a tension regulator may undergo. For instance, tension regulator 550 may elastically deform an amount corresponding to the difference between the non-deformed state shown in FIG. 6 and the deformed shape shown in FIG. 8, according to an exemplary embodiment. The amount of elastic deformation a tension regulator may undergo may be determined, at least in part, by the material of a tension regulator and geometry of a tension regulator, according to an exemplary embodiment. Further, tension regulators of the exemplary embodiments described herein may be designed to apply a tension to an actuation element, such as in the states shown in the exemplary embodiments of FIGS. 9 and 10, to remove slack but not apply an excessive amount of tension, which could overstress an actuation element.

Figure 11:
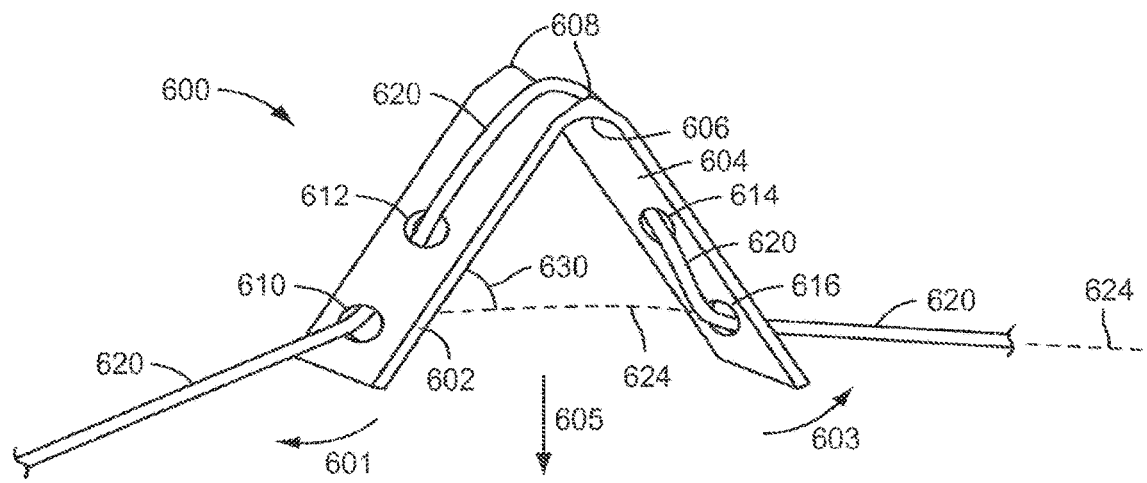
FIG. 11 depicts a tension regulator coupled to an actuation element in a slack state, according to another exemplary embodiment.

Other configurations may be used for the tension regulators of the exemplary embodiments described herein. Turning to FIG. 11, a tension regulator 600 is shown coupled to an actuation element 620. Tension regulator 600 may be fastened to actuation element 620 so that tension regulator 600 moves with actuation element 620, as described above with regard to the exemplary embodiment of FIG. 3. FIG. 11 depicts tension regulator 600 in a non-deformed state. Tension regulator 600 may be made of, for example, stainless steel or other surgical instrument materials familiar to one of ordinary skill in the art. According to an exemplary embodiment, apex 606 may be shaped to resist actuation element 620 slipping off of apex 606. For example, apex 606 may include projections 608 on lateral sides of actuation element 620, as shown in the exemplary embodiment of FIG. 11.

Tension regulator 600 may be coupled to actuation element 620 by threading actuation element 620 through holes 610 and 612 in a first leg 602, over an apex 606, and through holes 614 and 616 in a second leg 604 of tension regulator 600. Thus, when actuation element 620 is taut, substantially straight, and lacks slack, first leg 602 and second leg 604 may be bent (e.g., elastically deformed) along respective directions 601 and 603 relative to apex 606 and apex 606 may be pulled along direction 605 relative to a longitudinal axis 624 of actuation element 620, as shown in the exemplary embodiment of FIG. 11. As a result, the potential energy of tension regulator 600 may be increased and used to dynamically compensate for slack that develops in actuation element 620. When actuation element 620 is taut and lacks slack, actuation element 620 may be substantially straight and follow a path extending along (e.g., substantially coaxial with) axis 624, as discussed above with regard to the exemplary embodiment of FIG. 8. As actuation element 620 develops slack, tension regulator 600 may divert actuation element 620 from the path along axis 624. For example, tension regulator 600 may divert the portion of actuation element 620 extending through tension regulator 600 along a path forming a non-zero angle 630 relative to axis 624. Thus, tension regulator 600 may accommodate slack in actuation element 620 by increasing the path length of actuation element 620. In another example, tension regulator 600 may pull actuation element 620 along a direction that is substantially transverse (e.g., perpendicular) to longitudinal axis 624.

Figure 12:
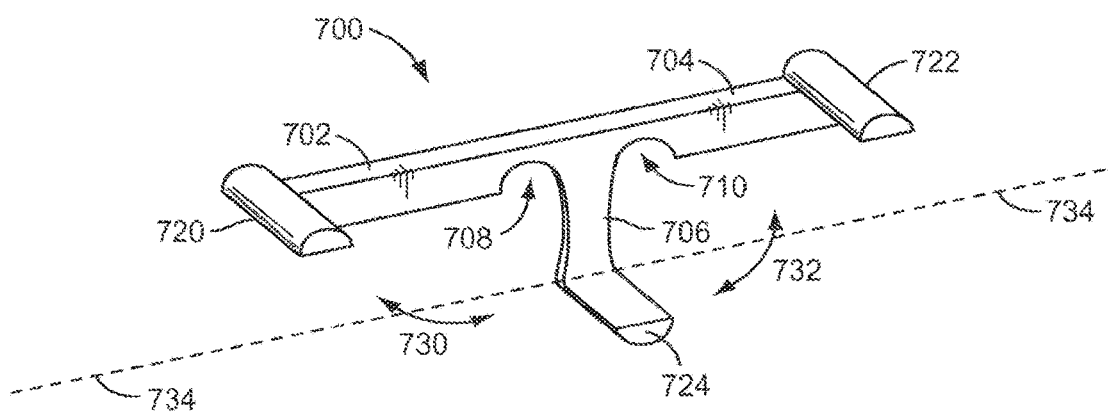
FIG. 12 depicts a tension regulator, according to yet another exemplary embodiment.

Another exemplary embodiment of a tension regulator 700 is shown in FIG. 12. Tension regulator 700 may comprise a first leg 702 and a second leg 704, with contact portions 720, 722 at respective ends of first and second legs 702, 704. Tension regulator 700 may further comprise a main leg 706 including a contact portion 724. An actuation element (not shown) may be threaded, for example, over contact portions 720, 722 at ends of legs 702, 704 and under contact portion 724. According to an exemplary embodiment, first and second legs 702, 704 may be configured to bend (e.g., elastically deform) relative to main leg 706. For example, first and second legs 702, 704 may include an area of material weakness, such as cutouts 708 and 710, to facilitate first and second legs 702, 704 bending relative to main leg 706, such as along directions 730 and 732 in the exemplary embodiment of FIG. 12. Thus, tension regulator 700 may experience a change in potential energy as tension regulator 700 is bent, which may be used to dynamically compensate for slack in an actuation element.

According to an exemplary embodiment, when an actuation element to which tension regulator 700 is coupled lacks slack (e.g., is taut and substantially straight along a path extending along axis 734 in FIG. 12), the actuation element may cause legs 702, 704 to bend along directions 730, 732 towards main leg 706. As the actuation element develops slack, tension regulator 700 may relax and legs 702, 704 may bend away from main leg 706. For example, tension regulator 700 may accommodate slack in an actuation element by diverting a path of actuation element from the path along axis 734, similar to the exemplary embodiments of FIGS. 8-10. As a result, tension regulator 700 may increase a path length of the actuation element relative to its longitudinal axis 734.

Figure 13:
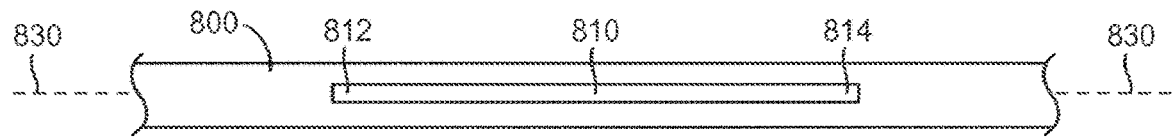
FIG. 13 depicts a tension regulator coupled to a force transmission element in a taut state, according to another exemplary embodiment.
Figure 14:
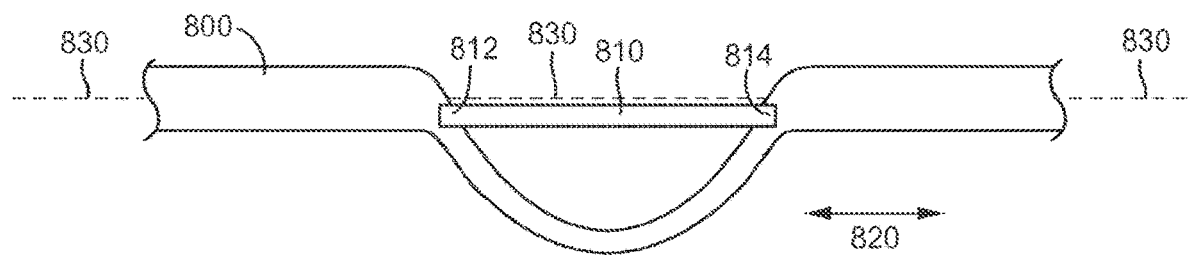
FIG. 14 depicts the tension regulator and actuation element of FIG. 13 in a slack state.

Turning to FIG. 13, another exemplary embodiment of a tension regulator 810 is depicted. Tension regulator 810 is coupled to an actuation element 800, such as by joining a first end 812 and a second end 814 of tension regulator 810 to actuation element 800. Tension regulator 810 may be a band of elastic material, according to an exemplary embodiment. FIG. 13 depicts a state in which actuation element 800 is taut and lacks slack. As a result, tension regulator 810 is elastically deformed and stretched along actuation element 800, as shown in the exemplary embodiment of FIG. 13. As actuation element 800 develops slack, as depicted in the exemplary embodiment of FIG. 14, tension regulator 810 may relax along the directions indicated by arrows 820 in FIG. 14 to compensate for the slack and keep actuation element 800 taut. Similar to the exemplary embodiments of FIGS. 6-10, tension regulator 810 may accommodate slack in actuation element 800 by diverting a path of actuation element 800 relative to an axis 830 that actuation element 800 extends along when actuation element 800 is taut and substantially straight, as depicted in FIG. 13. For example, tension regulator 810 may increase a length of the path of actuation element 800 relative to axis 830.

As described above with regard to the exemplary embodiment of FIG. 3, a tension regulator may be fastened to an actuation element so the tension regulator moves with the actuation element as the actuation element is paid out or wound upon an actuation input mechanism. According to an exemplary embodiment, contact surfaces of a tension regulator may be configured so that the tension regulator is fastened to the actuation element but if the tension regulator contacts a component of a force transmission mechanism (e.g., chassis portion 322 or actuation input mechanism 330, 332 in FIG. 3) as the actuation element is paid out or wound, the actuation element may be permitted to slide relative to the tension regulator to minimize or prevent damage to the tension regulator and force transmission mechanism components. For example, surfaces of loops 551, 553, 555 of tension regulator 550 in the exemplary embodiment of FIG. 6 may be smooth to permit an actuation element to slide relative to tension regulator 550 when tension regulator 550 impacts a force transmission mechanism component. Surfaces of tension regulators 600, 700, 800 of the exemplary embodiments of FIGS. 11-14 may also permit an actuation element to slide. According to an exemplary embodiment, surfaces of tension regulators may be shaped to minimize wear of an actuation element due to sliding against a tension regulator, such as by shaping tension regulator surfaces have large radii of curvature.

Figure 15:
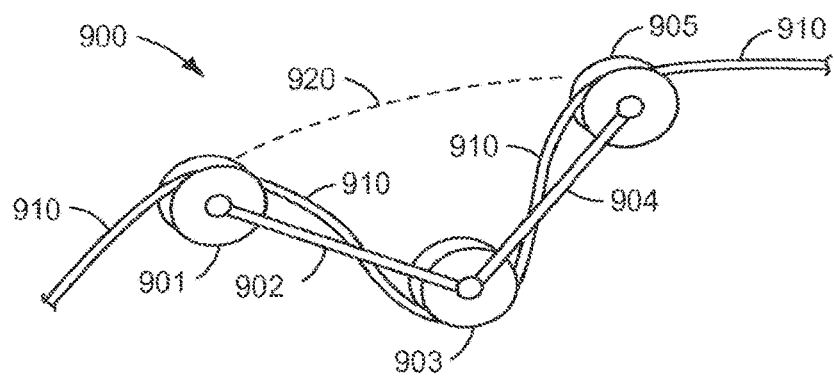
FIG. 15 depicts a tension regulator coupled to an actuation element in a slack state, according to another exemplary embodiment.

Turning to FIG. 15, an exemplary embodiment of a tension regulator 900 is shown that includes surfaces that couple tension regulator 900 to an actuation element 910 but permit tension regulator 900 to slide relative to actuation element 910, such as when tension regulator 900 impacts a component of a force transmission mechanism. Tension regulator 900 may comprise a first leg 902 and a second leg 904 connected to a main pulley 903, with pulleys 901 and 905 disposed at ends of first and second legs 902, 904. First and second legs 902, 904 may bend (e.g., elastically deform) relative to main pulley 903, similar to the exemplary embodiments of FIGS. 6-11. Actuation element 910 may be threaded through pulleys 901, 903, 905 so that tension regulator 900 is coupled to actuation element 910 but when tension regulator 900 impacts a force transmission mechanism component (e.g., chassis portion 322 or actuation input mechanism 330, 332 of FIG. 3), tension regulator 900 is permitted to slide relative to actuation element 910. According to an exemplary embodiment, as actuation element 910 develops slack, tension regulator 900 may divert a path of actuation element 910 relative to an axis 920 of actuation element 910 (e.g., a path along which actuation element 910 extends when actuation element 910 is taut and substantially straight), similar to the exemplary embodiments of FIGS. 6-10. As a result, tension regulator 900 may increase a path length of actuation element 910 relative to axis 920, according to an exemplary embodiment.

Figure 16:
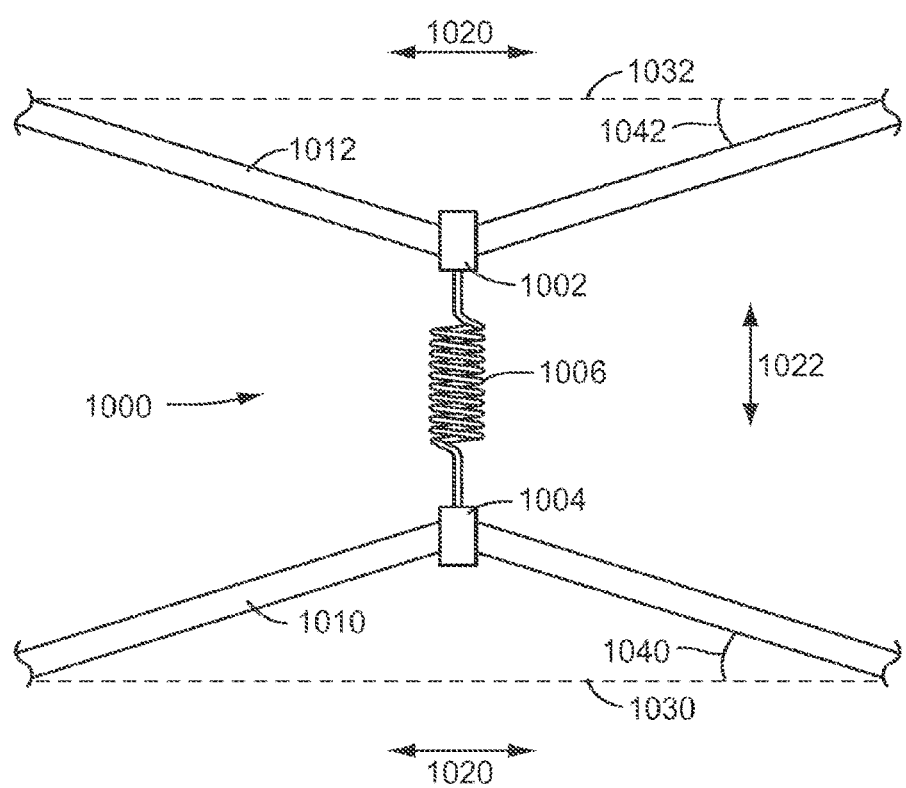
FIG. 16 depicts a tension regulator coupled to two actuation elements, according to an exemplary embodiment.

As discussed above with regard to the exemplary embodiments of FIGS. 4-15, a tension regulator may be coupled to a single actuation element. However, the tension regulators of the various exemplary embodiments described herein are not limited to being coupled to a single actuation element. Turning to FIG. 16, a tension regulator 1000 is shown coupled to a first actuation element 1010 and a second actuation element 1012. Actuation elements 1010, 1012 may be coupled to the same actuation input mechanism (e.g., actuation input mechanism 330 or 332 in the exemplary embodiment of FIG. 3). Tension regulator 1000 may comprise a first end 1002 coupled to actuation element 1012 and a second end 1004 coupled to actuation element 1010, with ends 1002, 1004 configured to slide relative to actuation elements 1010, 1012 as actuation elements 1010, 1012 are moved along the directions indicated by arrows 1020 in the exemplary embodiment of FIG. 16. Tension regulator 1000 may comprise a deformable portion 1006 to facilitate deformation (e.g., elastic deformation) of tension regulator 1000 along the directions indicated by arrows 1022 in FIG. 16, which facilitates compensation for slack in one or both of actuation elements 1010, 1012. Deformation portion 1006 may be, for example, a compliant portion of tension regulator 1000 that is more readily deformable that the remainder of tension regulator 1000, may be formed as a spring, or may have other configurations to facilitate elastic deformation of tension regulator 1000.

According to an exemplary embodiment, when actuation elements 1010, 1012 are taut and lack slack (e.g., prior to developing slack), actuation elements 1010, 1012 may extend along a path along axes 1030, 1032. In such a state, deformation portion 1006 is stretched (e.g., via elastic deformation) tension regulator 1000 experiences an increase in potential energy. As actuation elements 1010, 1012 develop slack, deformation portion 1006 may relax and tension regulator 1000 may divert actuation elements 1010, 1012 from a path along (e.g., substantially coaxial to) their respective axes 1030, 1032, similar to the exemplary embodiments of FIGS. 8-10, to compensate for the slack. For example, portions of actuation elements 1010, 1012 extending through ends 1002, 1004 may form non-zero angles with the axes 1030, 1032.

As discussed above with regard to the exemplary embodiments of FIGS. 3-16, a tension regulator may be coupled to an actuation element so that the tension regulator moves with the actuation element. Thus, the tension regulator moves relative to the chassis of a force transmission mechanism when the actuation element is paid out and wound upon an actuation input mechanism. The various exemplary embodiments described herein are not limited to such tension regulators and may also include tension regulators fixed to the chassis of a force transmission mechanism.

Figure 17:
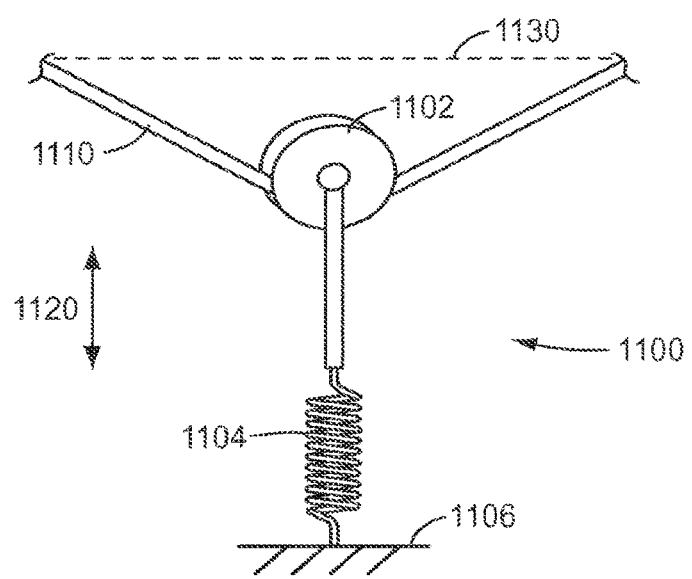
FIG. 17 depicts a tension regulator mounted to a force transmission mechanism and coupled to an actuation element, according to an exemplary embodiment.

Turning to FIG. 17, an exemplary embodiment of a tension regulator 1100 is shown that is fixed to a portion 1106 (e.g., chassis 320 in FIG. 3) of a force transmission mechanism. Tension regulator 1100 may be coupled to an actuation element 1110, such as by extending actuation element 1110 through a pulley 1102 or other member of tension regulator 1100 that couples tension regulator 1100 to actuation element 1110. Tension regulator 1100 may further comprise a deformable portion 1104 to facilitate deformation of tension regulator 1100 along the directions indicated by arrows 1120 in FIG. 17, which facilitates compensation for slack in actuation element 1110. Deformation portion 1104 may be, for example, a compliant portion of tension regulator 1100 that is more readily deformable that the remainder of tension regulator 1100, may be formed as a spring, or may have other configurations to facilitate elastic deformation of tension regulator 1100. When actuation element 1110 lacks slack, actuation element 1110 may follow a path along (e.g., substantially coaxial to) the axis 1130 of actuation element 1110, as discussed above with regard to the exemplary embodiments of FIGS. 8-10. As actuation element 1110 develops slack, tension regulator 1100 may pull actuation element 1110, such as along a direction transverse (e.g., perpendicular to axis 1130). Thus, the path of actuation element 1110 differs from the path along axis 1130 when actuation element 1110 is taut and has not developed slack, similar to the exemplary embodiment of FIGS. 8-10. As a result, tension regulator 1100 may increase a path length of actuation element 1110 as slack is developed in actuation element 1110.

A tension regulator may have a single piece (e.g., monolithic) construction. A tension regulator having a single piece (e.g., monolithic) construction may be efficient to manufacture and couple to an actuation element but also effective for slack compensation. As shown in the exemplary embodiment of FIGS. 6 and 7, Tension regulator 550 may have a single piece (e.g., monolithic) construction. For example, tension regulator 550 may be, for example, a single piece of wire. Tension regulator 600 of the exemplary embodiment of FIG. 11 may also have a single piece (e.g., monolithic) construction. For example, tension regulator 600 may be a single piece of sheet metal having the shape shown in the exemplary embodiment of FIG. 11. Another exemplary embodiment of a tension regulator that may have a single piece (e.g., monolithic) construction is tension regulator 700 of FIG. 12. Tension regulator 700 may be molded as a single piece, for example. Tension regulator 810 of the exemplary embodiment of FIGS. 13 and 14 may also have a single piece (e.g., monolithic) construction. According to an exemplary embodiment, tension regulator 1000 of FIG. 16 may have a single piece (e.g., monolithic) construction that comprises ends 1002, 1004 and deformation portion 1006.

Although tension regulators of the various exemplary embodiments contemplated herein have been described with reference to actuation elements within a force transmission mechanism of a surgical instrument, tension regulators of the various exemplary embodiments described herein are not limited to use with a force transmission mechanism of an instrument. For example, tension regulators of the various exemplary embodiments described herein may be coupled to actuation elements of a patient side cart of teleoperated surgical system. According to an exemplary embodiment, tension regulators of the various exemplary embodiments described herein may be coupled to actuation elements (e.g., tension elements) used to actuate manipulator arms 110-113 of patient side cart 100 of the exemplary embodiment of FIG. 1. Thus, tension regulators of the various exemplary embodiments described herein may be coupled to actuation elements within manipulator arms 110-113, not only to actuation elements located within force transmission mechanism 134 of FIG. 1.

By providing a force transmission mechanism comprising a tension regulator, slack of an actuation element may be compensated. Further, the tension regulator may have a simple design that is efficient to manufacture and couple to an actuation element, while being capable of compensating for slack of the actuation element.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. An instrument comprising:
a shaft;
a moveable component coupled to the shaft;
a force transmission assembly coupled to the shaft, the force transmission assembly comprising:
one or more cables;
a rotary input drive member operably coupled to the one or more cables and configured to transmit a drive force to actuate the moveable component;
a passive tension regulator mechanism comprising a first pulley and a second pulley connected via a linkage,
wherein a first cable of the one or more cables is coupled to the rotary input drive member and routed at least partially around the first pulley and the second pulley of the passive tension regulator mechanism, and
wherein the linkage pivotally rotates the second pulley about the first pulley in response to slack development in the first cable so as to maintain tension in the first cable.

2. The instrument of claim 1,
wherein the passive tension regulator mechanism is configured to generate a biasing force that urges movement of the second pulley, and
wherein in response to slack development in the first cable, the biasing force pivotally rotates the second pulley about the first pulley.

3. The instrument of claim 1,
wherein the one or more cables comprise a second cable coupled to the rotary input drive member and the movable component, the second cable configured to transmit the drive force from the rotary input drive member to the movable component.

4. The instrument of claim 3,
wherein pivotal rotation of the second pulley about the first pulley in response to slack development in the first cable maintains tension in the second cable.

5. The instrument of claim 1,
wherein the passive tension regulator mechanism further comprises a third pulley connected to the first pulley via a second linkage, the second linkage configured to pivotally rotate the third pulley about the first pulley.

6. The instrument of claim 1, further comprising:
a wrist, an end effector, or both the wrist and the end effector;
wherein the moveable component comprises the wrist or the end effector.

7. The instrument of claim 1,
wherein the force transmission assembly is removably mountable to an actuation interface assembly of a teleoperable surgical system, and
wherein the rotary drive input member is configured to operably couple to a rotary drive output member of the actuation interface assembly in a mounted state of the force transmission assembly to the actuation interface assembly.

8. An instrument comprising:
a shaft;
a moveable component coupled to the shaft;
a force transmission assembly coupled to the shaft, the force transmission assembly comprising:
one or more cables;
a rotary input drive member operably coupled to the one or more cables and configured to transmit a drive force to actuate the moveable component;
a passive tension regulator mechanism comprising a first pulley and second pulley connected via a linkage,
wherein a first cable of the one or more cables is coupled to the rotary input drive member and routed at least partially around the first pulley and the second pulley of the passive tension regulator mechanism, and
wherein the linkage of the passive tension regulator mechanism is biased so as to rotate the second pulley pivotally about the first pulley to maintain tension in the first cable.

9. The instrument of claim 8,
wherein the one or more cables comprise a second cable coupled to the rotary input drive member and the movable component, the second cable configured to transmit the drive force from the rotary input drive member to the movable component.

10. The instrument of claim 9,
wherein the linkage of the passive tension regulator mechanism is biased so as to rotate the second pulley pivotally about the first pulley to maintain tension in the second cable.

11. The instrument of claim 8,
wherein the passive tension regulator mechanism further comprises a third pulley connected to the first pulley via a second linkage, the second linkage configured to pivotally rotate the third pulley about the first pulley.

12. The instrument of claim 8, further comprising:
a wrist, an end effector, or both the wrist and the end effector;
wherein the moveable component comprises the wrist or the end effector.

13. The instrument of claim 8,
wherein the force transmission assembly is removably mountable to an actuation interface assembly of a teleoperable surgical system, and
wherein the rotary drive input member is configured to operably couple to a rotary drive output member of the actuation interface assembly in a mounted state of the force transmission assembly to the actuation interface assembly.

14. An instrument comprising:
a shaft;
a moveable component coupled to the shaft;
a force transmission assembly coupled to the shaft, the force transmission assembly comprising:
a first rotary input drive member operably coupled to transmit a drive force to actuate the moveable component in a first motion;
a second rotary input drive member operably coupled to transmit a drive force to actuate the moveable component in a second motion;
a cable operably coupled to the first rotary input drive member and the second rotary input drive member; and
a passive tension regulator mechanism coupled to a length of the cable between the first and second rotary input drive members, the passive tension regulator mechanism comprising a first pulley and a second pulley connected via a linkage, the linkage configured to pivotally rotate the second pulley about the first pulley, wherein the cable is routed at least partially around the first pulley and the second pulley, and wherein the second pulley pivotally rotates about the first pulley in response to slack development in the cable so as to maintain tension in portions of the cable between the passive tension regulator mechanism and each of the first and second rotary input drive members.

15. The instrument of claim 14, wherein the passive tension regulator mechanism is configured to generate a biasing force that urges movement of the second pulley, and wherein in response to slack development in the cable, the biasing force pivotally rotates the second pulley about the first pulley.

16. The instrument of claim 14, further comprising:

a second cable coupled to one of the first and second rotary input drive members and coupled to the movable component to transmit the drive force to actuate the moveable component.

17. The instrument of claim 16, wherein the pivotal rotation of the second pulley about the first pulley in response to slack development in the cable maintains tension in the second cable.

18. The instrument of claim 14, wherein the passive tension regulator mechanism further comprises a third pulley connected to the first pulley via a second linkage, the second linkage configured to pivotally rotate the third pulley about the first pulley.

19. The instrument of claim 14, wherein the moveable component comprises a wrist, an end effector, or an end effector coupled to a wrist.

20. The instrument of claim 14, wherein the force transmission assembly is mountable to an actuation interface assembly of a teleoperable surgical system, and wherein the first and second rotary drive input members are configured to operably couple to first and second rotary drive output members, respectively, of the actuation interface assembly in a mounted state of the force transmission assembly to the actuation interface assembly.

* * * * *